United States Patent [19]

Andén et al.

[11] Patent Number: 5,635,537
[45] Date of Patent: Jun. 3, 1997

[54] 8-SUBSTITUTED-2-AMINOTETRALINS

[75] Inventors: Nils-Erik Andén, Spånga; Berit C. E. Backlund Höök, Uppsala; Anna L. Björk, Uppsala; Uli A. Hacksell, Uppsala; Sven-Erik Hillver, Uppsala; Ye Liu, Uppsala; Eva C. Mellin, Uppsala; Eva M. Persson, Uppsala; Karl J. Vallgårda, Uppsala; Hong Yu, Uppsala, all of Sweden

[73] Assignee: Astra Aktiebolag, Sodertalje, Sweden

[21] Appl. No.: 33,013

[22] Filed: Mar. 18, 1993

Related U.S. Application Data

[63] Continuation of Ser. No. 525,541, May 18, 1990, abandoned.

[30] Foreign Application Priority Data

May 26, 1989 [SE] Sweden ................. 8901889

[51] Int. Cl.$^6$ ............ A61K 31/135; C07C 225/20; C07D 307/52; C07D 333/04
[52] U.S. Cl. ............ 514/657; 514/427; 514/429; 514/438; 514/461; 514/226.5; 514/255; 514/278; 514/319; 514/326; 514/328; 514/412; 514/414; 514/415; 544/33; 544/392; 546/16; 546/19; 546/205; 546/206; 546/207; 546/208; 546/212; 546/213; 546/214; 548/517; 548/525; 548/465; 548/364.7; 548/364.1; 548/365.7; 548/365.1; 548/361.5; 548/362.5; 548/306.1; 548/305.1; 548/312.1; 548/314.7; 549/80; 549/504; 564/374; 564/428
[58] Field of Search ............ 544/33, 392; 564/374, 564/428; 546/208, 16, 19, 205, 206, 207, 212, 213, 214; 548/517, 525, 465, 364.7, 64.1, 365.7, 361.5, 362.5, 306.1, 305.1, 312.1, 314.7; 514/226.5, 255, 278, 412, 414, 415, 326, 319, 328, 657, 654, 438, 461, 417, 429; 569/80.504

[56] References Cited

U.S. PATENT DOCUMENTS 4,876,284 10/1989 Arvidsson et al. .......... 564/428

FOREIGN PATENT DOCUMENTS 0 11721  6/1980 European Pat. Off. ..
0041488 12/1981 European Pat. Off. ..
0168505  1/1986 European Pat. Off. ..
0209275  1/1987 European Pat. Off. ..
0270947  6/1988 European Pat. Off. ..
0272534  6/1988 European Pat. Off. ..
2752659  6/1978 Germany .
WO0015047 12/1990 WIPO .

OTHER PUBLICATIONS

Peroutka, S.J. "Pharmacological Differentiation and Characterization of 5-HT$_{1A}$, 5-HT$_{1B}$ and 5-HT$_{1C}$ Binging Sites in Rat Frontal Cortex", J. Neurochem., 47: 529–540, 1986.

Hammon et al. "The central 5HT1A receptors:pharmacological, biochemical, functional, and regulatory properties" N. Y. Aca. Scien. v. 600, p. 114–131 1990.

Gotto et al "The Role of Receptors in Biology & Medicine" Raven Press, p. 191 (1986).

Glennon "Central Serotomine Receptors as targets for dry research" J. Med. Chem. 30 1–12 (1987).

Aridsson et al "5–hydroxtryptamine receptors Agonists" J. Med. Chem. 27 45–51 (1984).

Primary Examiner—Ceila Chang
Attorney, Agent, or Firm—White & Case

[57] ABSTRACT

A compound of the formula

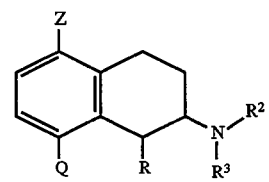

Z is hydrogen or halogen, Q is COR$^1$ or 5-or 6-membered aryl which may contain 1 or 2 heteroatoms selected from N, 0 or S and may be substituted or fused wherein R is hydrogen or C$_1$-methyl (cis-configuration), R$^1$ is C$_1$–C$_6$ alkyl or an aromatic ring which may contain heteroatoms selected from O and S and may be substituted or fused to an optionally substituted benzene ring, R$^2$ is hydrogen or C$_1$–C$_6$ alkyl and R$^3$ may be different groups defined in claim 1, and enantiomers/salts thereof, processes for preparation of said compounds, pharmaceutical preparations containing said compounds, use of and method of treatment of disorders in CNS by using said compounds.

7 Claims, No Drawings

8-SUBSTITUTED-2-AMINOTETRALINS

This application is a continuation of application Ser. No. 07/525,541, filed on May 18, 1990, now abandoned.

FIELD OF THE INVENTION

The present invention relates to novel 8-carbonyl-aryl-substituted 2-aminotetralines, enantiomers and salts thereof, processes for their preparation, pharmaceutical compositions containing said compounds and to the use of said compounds in therapy.

An object of the invention is to provide compounds for therapeutic use, especially compounds having a therapeutic activity via the central nervous system (CNS). A further object is to provide compounds having a selective effect on the 5-hydroxy-tryptamine receptors in mammals including man.

PRIOR ART

Therapeutically useful tetraline derivatives having effect on 5-hydroxy tryptamine neurons in mammals are disclosed in EP 41 488, EP 270 947 and EP 272 534.

DISCLOSURE OF THE INVENTION

The object of the present invention is to obtain new compounds which have a high affinity to the 5-hydroxy-tryptamine receptors in the central nervous system at the same time as they act as agonists, partial agonists or antagonists on the serotonin receptors.

Thus, the new compounds of the formula I of the present invention as well as the enantiomers and salts thereof are useful in therapeutic treatment of 5-hydroxy-tryptamine mediated states and disorders such as depression, anxiety, anorexia, senile dementia, Alzheimer's disease, migraine, termoregulator and sexual disturbances. Further aspects of the invention are related to the use of the compounds, enantiomers and salts thereof in pain control and in modulation of the cardiovascular system.

Thus, the invention provides compounds of the formula

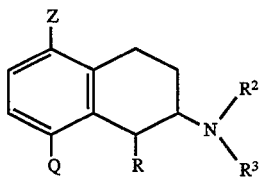

(I)

wherein

R is hydrogen or methyl with the proviso that the $C_1$-methyl substituent is in cis-configuration, Z is hydrogen or halogen, Q is $COR^1$ or a 5- or 6-membered-aryl which may contain 1 or 2 heteroatoms selected from N, O or S and being either (i) optionally substituted by one or/more substituents independently selected from halogen, CN, $CF_3$, $C_1$–$C_6$ alkyl, $C_2$–$C_6$ alkenyl or lower alkoxy or either (ii) fused at two adjacent carbon atoms to an aryl ring, said aryl ring being optionally substituted by one or more substituents independently selected from halogen, CN, $CF_3$, $C_1$–$C_6$ alkyl, $C_2$–$C_6$ alkenyl or lower alkoxy, $R^1$ is $C_1$–$C_6$ alkyl or a 5- or 6-membered aromatic ring which may contain heteroatoms selected from O and S and being either (i) optionally substituted by substituents independently selected from halogen, $CF_3$, lower alkyl or lower alkoxy or either (ii) fused at two adjacent carbon atoms to a benzene ring, said benzene ring being optionally substituted by substituents independently selected from halogen, $CF_3$, lower alkyl or lower alkoxy, $R^2$ is hydrogen or $C_1$–$C_6$ alkyl, $R^3$ is a group $C_1$–$C_6$ alkyl,

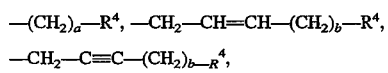

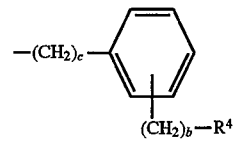

or

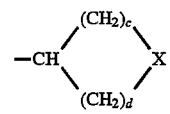

where a is 1 to 5, b is 0, 1 or 2, c is 1, 2, 3 or 4, d is 2 or 3,

X is O, S or $NR^5$, where $R^5$ is hydrogen, cycloalkyl, alkyl, $C_1$—$C_6$—alkyl, optionally substituted with hydroxy, amino, alkylamino, dialkylamino, carbamoyl or sulfamoyl, aryl, heteroaryl, aralkyl, alkoxycarbonyl, alkylsulfonyl, phenylsulfonyl, tolylsulfonyl, benzylsulfonyl, formyl, carbamoyl or sulfamoyl, $R^4$ is hydrogen, halogen, $CF_3$, CN or a group —$OR^6$, —$COOR^7$, —$CONR^8R^9$, —$SO_2NR^8R^9$, —$SO_mR^{10}$, —$NR^{11}R^{12}$,

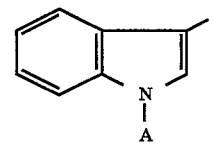

or

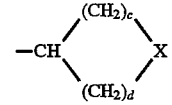

where c, d and X have the meaning given above,

A is hydrogen, alkylsulfonyl, phenylsulfonyl, tolylsulfonyl, benzylsulfonyl, acyl or alkoxycarbonyl, $R^6$ is hydrogen, alkyl, alkenyl, cycloalkyl, aryl, aralkyl, acyl, alkoxycarbonyl, aryloxycarbonyl, $R^7$ is hydrogen, alkyl, alkenyl, aryl or aralkyl, $R^8$ and $R^9$ which are the same or different are each hydrogen, alkyl, aryl or aralkyl, $R^{10}$ is alkyl, cycloalkyl, aryl or aralkyl and the aryl residue may be substituted with halogen, cyano, alkyl, alkoxy, trifluormethyl or trifluormethoxy, m is 0, 1 or 2

$R^{11}$ and $R^{12}$ which are the same or different are each hydrogen, alkyl, aryl or aralkyl, and the aryl residue may be substituted with halogen, cyano, alkyl, alkoxy or trifluormethyl, or $R^{11}$ and $R^{12}$ together with the nitrogen atom form a ring:

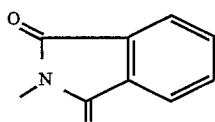

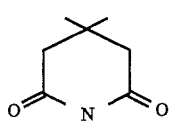

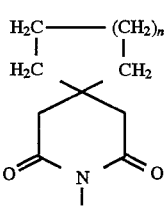

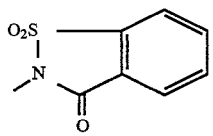

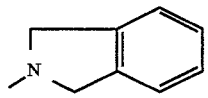

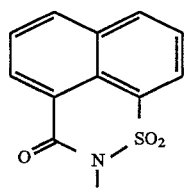

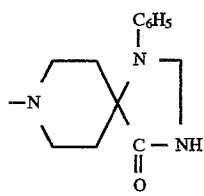

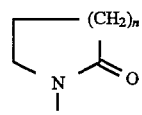

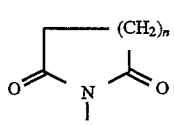

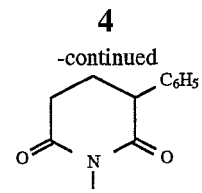

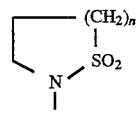

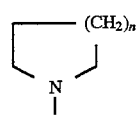

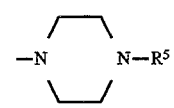

wherein n is 1 or 2, $R^2$ and $R^3$ together with the nitrogen atom form a ring of the formula

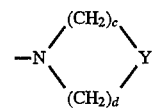

wherein c and d have the meaning given above, and

Y is O, S or a group $NR^5$ or $CH(CH_2)_e$—$NHR^5$, where $R^5$ has the meaning given above, and e is 0, 1, 2, 3 or 4, and enantiomers and physiologically acceptable salts thereof.

Alkyl in formula I representing straight or branched alkyl groups having 1 to 12 carbon atoms, for example methyl, ethyl, n-propyl, i-propyl, n-butyl, i-butyl, t-butyl, n-pentyl, i-pentyl, n-hexyl, i-hexyl, n-heptyl, i-heptyl, n-octyl and i-octyl. Preferred alkyl groups are alkyl groups having 1 to 5 carbon atoms.

$C_1$–$C_6$ alkyl in formula I representing straight, branched and cyclic alkyl groups having 1–5 carbon atoms, for example methyl, ethyl, n-propyl, i-propyl, n-butyl, i-butyl, t-butyl, n-pentyl, i-pentyl, t-pentyl, cyclopropyl, cyclobutyl, cyclopentyl, methylcyclopropyl, ethylcyclopropyl, methylcyclobutyl. Preferred alkyl groups are alkyl groups having 1 to 4 carbon atoms.

Lower alkyl in formula I representing straight alkyl groups having 1 to 4 carbon atoms, for example methyl, ethyl, n-propyl or n-butyl, preferably ethyl, n-propyl.

Cycloalkyl in formula I representing cyclic carbon atom chain having 5 to 8 carbon atoms, for example cyclopentyl, cyclo-hexyl, cycloheptyl and cyclooctyl.

Alkenyl in formula I representing straight or branched carbon atoms chains having 2 to 12 carbon atoms and containing one or two double bond, for example allyl, propenyl, isopropenyl, butenyl, isobutenyl, pentenyl, isopentenyl, hexanyl, isohexanyl, heptanyl, isoheptanyl, octanyl and isooctanyl. Preferred alkenyl groups have 2 to 4 carbon atoms and one double bond.

$C_2$-$C_6$ alkenyl in formula I representing straight or branched carbon atom chains having 2 to 6 carbon atoms and containing one or two double bonds, for example allyl, propenyl, isopropenyl, butenyl, isobutenyl, pentenyl, isopentenyl. Preferred alkenyl groups have 2 to 4 carbon atoms and one double bond.

Alkoxy in formula I representing straight or branched carbon atom chains having 1 to 12 carbon atoms, preferably 1 to 4 carbon atoms, where the carbon chain is bond by an oxygen atom. For example methoxy, ethoxy propoxy, isopropoxy, butoxy, isobutoxy, pentoxy, isopentoxy, hexoxy, isohexoxy, heptoxy, isoheptoxy, octoxy and isooctoxy.

Lower alkoxy in formula I representing a straight alkoxy group having 1 to 4 carbon atoms, for example methoxy, ethoxy, propoxy or butoxy, preferably methoxy and ethoxy.

5- or 6-membered aryl which may contain 1 or 2 heteroatoms selected from N, O or S and being either (i) optionally substituted by one or more substituents independently selected from halogen, CN, $CF_3$, $C_1$-$C_6$ alkyl, $C_2$-$C_6$ alkenyl or lower alkoxy or either (ii) fused at two adjacent carbon atoms to an aryl ring, said aryl ring being optionally substituted by one or more substituents independently selected from halogen, CN, $CF_3$, $C_1$-$C_6$ alkyl, $C_2$-$C_6$ alkenyl or lower alkoxy, in the definition of Q in formula I representing either (i) substituted or unsubstituted phenyl, thienyl, furyl, pyridyl, pyrimidyl, pyrazinyl, pyradazinyl, thiozolyl, isothiozolyl, oxazolyl, isoxazolyl, imidazolyl, pyrazolyl, piperazinyl or morpholinyl or either (ii) substituted or unsubstituted quinolyl, isoquinolyl, quinazolyl, quinaxazolyl or indolyl.

Acyl in formula I representing phenyl or straight or branched carbon atom chains having 1 to 6 carbon atoms, preferably 1 to 4 carbon atoms, bond by a carbonyl group, for example benzoyl, acetyl, ethylcarbonyl, propylcarbonyl, isopropylcarbonyl, butylcarbonyl and isobuturylcarbonyl.

Aryl in formula I representing an aromatic residue having 6 to 12 carbon atoms, for example phenyl, naphtyl and biphenyl.

Aralkyl in formula I representing an aryl residue having 7 to 14 carbon atoms bond by an alkylen chain, preferably the aralkyl residue having 1 to 6 carbon atoms in the aliphatic chain and 6 to 12 carbon atoms in the aromatic ring. For example benzyl, naphtylmethyl, phenethyl and phenylpropyl.

Alkoxy carbonyl in formula I representing a group

wherein alkyl is defined as above. Preferred alkoxy carbonyl groups having 1 to 4 carbon atoms in the alkyl chain, for example methoxy carbonyl, ethoxy carbonyl, propoxy carbonyl, isopropoxy carbonyl, butoxy carbonyl and isobutoxy carbonyl.

Halogen in formula I representing fluor, chlor, brom, iod, preferably fluor, chlor and brom, especially fluor.

Examples of suitable 5-or 6-membered aromatic rings which contain atoms selected from C, O or S are phenyl, thienyl and furanyl. Example of a suitable 5- or 6-membered aromatic ring containing C, O or S atoms which are fused at two adjacent carbon atoms is benzofuran.

The compounds of the invention have one or two asymmetric carbon atoms. When R is hydrogen the compounds have an asymmetric carbon atom adjacent to the nitrogen atom i.e. $C_2$ and when R is methyl the compounds have an asymmetric carbon atom adjacent to the nitrogen atom and an asymmetric carbon atom adjacent to the methyl group i.e. $C_1$ and $C_2$. Thus, the compounds exist as two or four stereo isomers i.e. enantiomers and/or diastereomers. Both the pure enantiomers and racemic mixtures are within the scope of the present invention. The therapeutic properties of the compounds may to a greater or lesser degree be ascribed to the racemate to the enantiomers occurring.

$C_1$-methylated derivatives of formula I where the methyl substituent is in cis configuration to the 2-amino substituent on $C_2$ has been found to e potent 5-hydroxytryptamine receptor agonists. Preferred compounds have a 1S, 2R-configuration.

Both organic and inorganic acids can be employed to form non-toxic physiologically acceptable acid addition salts of the compounds of this invention. Illustrative acids are sulfuric, nitric, phosphoric, oxalic, hydrochloric, hydrobromic, citric, acetic, lactic, tartaric, pamoic, ethanedisulfonic, sulfamic, succinic, cyclohexylsulfamic, fumaric, maleic and benzoic acids. These salts are readily prepared by methods known in the art.

Preferred compounds are those Q is phenyl, fluorophenyl, thienyl or furanyl or $COR^1$ wherein $R^1$ is $CH_3$, $C_2H_5$, $C_3H^7$, $C_4H_9$, $C_5H_{11}$, cyclopropyl, methylcyclopropyl, methylcyclobutyl, and $R^3$ is $C_{1-C6}$ alkyl, and R is hydrogen.

METHODS FOR PREPARATION

The compounds of the invention may be prepared by one of the following methods constituting a further aspect of the invention.

a. Converting a compound of the formula (II)

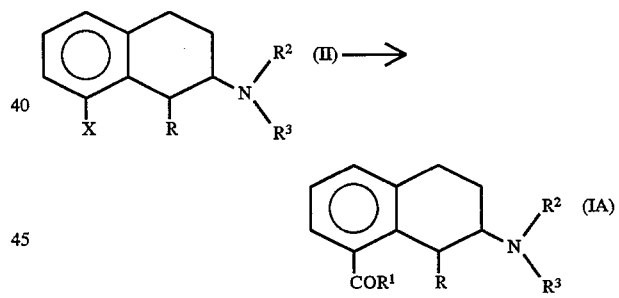

wherein X is a leaving group such as trifluoromethanesulfonate (Tf), phosphonate, halide such as Br or J, and R, $R^2$ and $R^3$ are defined as above by substitution of the group X to a carboxy group $COR^1$ to formation of a compound of formula IA.

The compound (II) can be converted to compound (IA) by the following catalytic cycle. Metal (M) should be a zerovalent transition metal $M^0$ such as Pd or Ni with ability to undergo oxidative addition to aryl-x-bonds e.g. the arylhalogen bonds. $M^0$ may be generated in situ from $M^{II}$ treatment with carbon monoxide (co). $M^1$ should be a metal such as Sn, Mg, Zn, Zr, B, Al, Li, which can undergo transmetallation with the initially formed carbonylated σ-aryl-metal-X-complex. (e.g. σ-aryl-metalhalide complex).

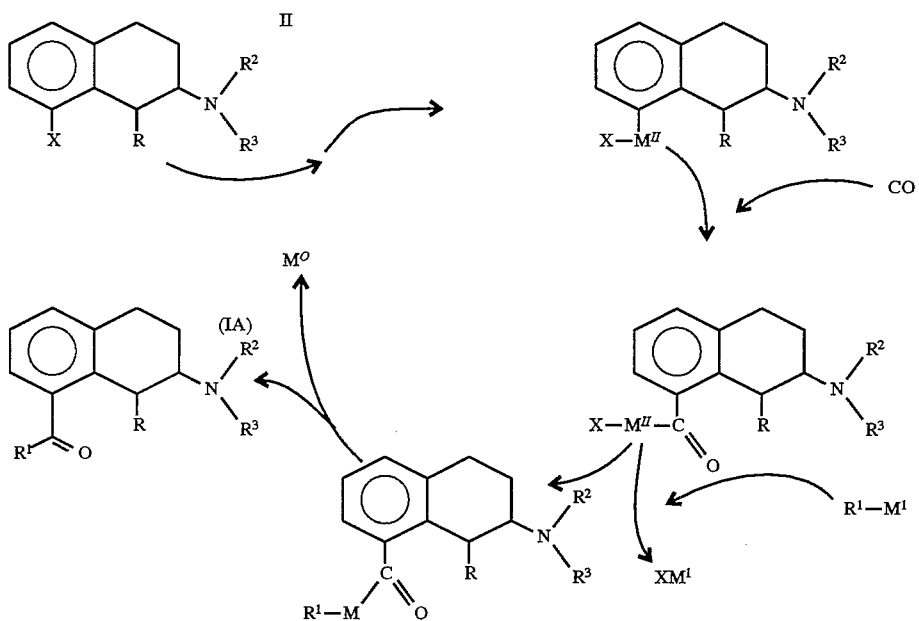

Further reagants are carbonmonoxide, an amine such as triethylamine in an inert organic solvent preferentially a polar aprotic solvent such as dimethylformamide (DMF), dimethylsulfoxide (DMSO), aceton, acetonitrile etc. The reaction is normally performed at a temperature between +40 to +120° C. and at a pressure between 1 to 5 bar. Finally it may be necessary to perform a catalytic hydrogenation (for instance by using $H_2$, Pd(C)) to obtain the desired $R^1$ group, e.g. to convert alkynes or alkenes to alkanes.

b) Compound (IA) can also be formed by the reversed process:

A reaction as the catalytic cycle using a zerovalent transition metal $M^0$ such as Pd or Ni with ability to undergo an oxidation addition to $R^1$-X, wherein $R^1$ defined as under formula IA and X is a leaving group such as halide, treatment with carbon monoxide followed by addition of a compound of formula III.

The $R^1$—CO—$M^{II}$—X can also be forked from $R^1$—COCl directly. The reaction conditions and reagant are the same as described in process a) above.

c) Converting a compound of the formula (II)

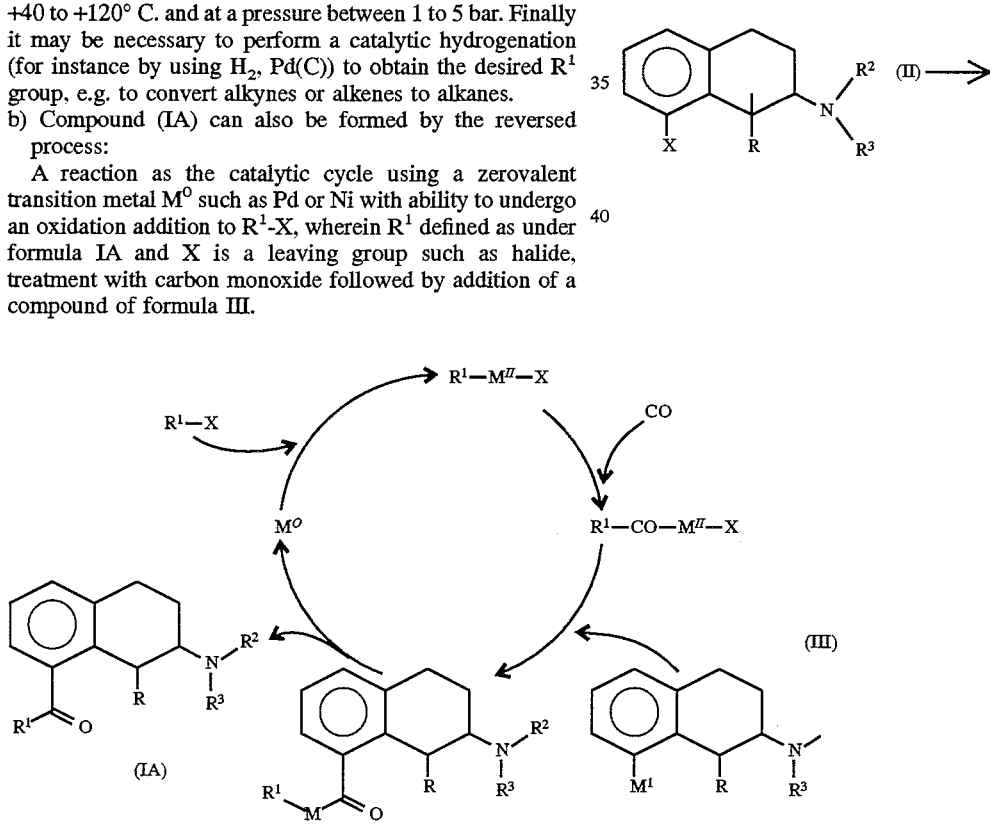

-continued

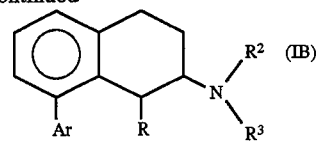

wherein X is a leaving group such as trifluoromethanesulphonate (Tf), phosponate, halide such as Br or J and R, $R^2$ and $R^3$ are defined as above by substitution of the group X to 5- or 6-membered aryl (Ar) which may contain 1 or 2 heteroatoms selected from N, O, or S being either substituted or fused at two adjacent carbon atoms to an aryl ring as defined above to formation of a compound of formula (IB).

The compound (II) may be converted to (IB) by reaction with a zerovalent transition metal $M^o$, such as Pd or Ni with ability to undergo oxidative addition to the aryl-X-bond. A suitable aryl-substituent can be introduced via a trialkylarylstannane.

Further reagents are an amine such as triethylamine and lithiumsalt e.g. lithium chloride. The reaction is preferentially carried out in a polar aprotic solvent such as dimethylformamide, dioxane, acetonitril or dimethylsulfoxide at a temperature between +40° to +120° C.

d) Converting a compound of the formula (V)

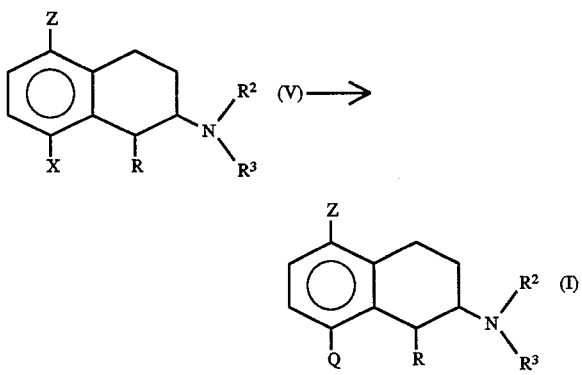

wherein X is a leaving group such as trifluoromethanesulphonate (Tf), Z is halogen and R, $R^2$, $R^3$ are defined as above by substitution of the group X to group Q which means a carboxy group $COR^1$ or a 5-or 6-membered aryl according to the above definitions and prepared as described in methods (a), (b) and (c).

e. Converting a compound of the formula (IV) (described in EP 272 534)

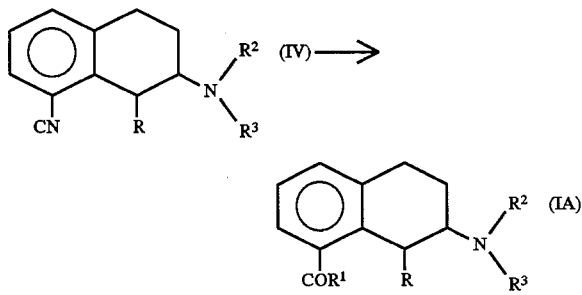

wherein $R^2$ and $R^3$ are defined as above by substitution of the nitrile to a carboxy group $COR^1$ to formation of a compound of formula IA. The reaction is carried out by treatment with an appropriate organometallic reagent preferentially organolithium or Gringard reagent in an inert organic solvent preferentially a nonpolar aprotic solvent such as ethers e.g. diethyl ether, tetrahydrofuran, benzen, followed by hydrolysis of the intermediate complex to obtain the desired compound.

PHARMACEUTICAL PREPARATIONS

According to the present invention the compounds of the formula I will normally be administered orally, rectally or by injection, in the form of pharmaceutical preparations comprising the active ingredient either as a free base or a pharmaceutically acceptable non-toxic acid addition salt, e.g. the hydrochloride, hydrobromide, lactate, acetate, phosphate, sulphate, sulphamate, citrate, tartrate, oxalate and the like in a pharmaceutically acceptable dosage form. The dosage form may be a solid, semisolid or liquid preparation. Usually the active substance will constitute between 0.1 and 99% by weight of the preparation, more specifically between 0.5 and 20% by weight for preparations intended for injection and between 0.2 and 50% by weight for preparations suitable for oral administration.

To produce pharmaceutical preparations containing a compound of the formula I in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the table can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compounds.

For the preparation of soft gelatine capsules, the active substance may be admixed with e.g. a vegetable oil or polyethylene glycol. Hard gelatine capsules may contain granules of the active substance using either the abovementioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain colouring agents, flavouring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from about 0.5% to about 10% by weight. These solutions may also contain stabilizing agents and/or buffering agents and may conveniently be provided in various dosage unit ampoules.

Suitable daily doses of the compounds of the invention in therapeutical treatment of humans are about 0.01–100 mg/kg bodyweight at peroral administration and 0.001–100 mg/kg bodyweight at parenteral administration.

WORKING EXAMPLES

Example 1

(±)-2-(Dipropylamino)-8-[(trifluoromethylsulfonyl)oxy]-tetralin

A solution of trifluoromethanesulphonic anhydride (7.0 g, 24.8 mmol) in dichloromethane (20 ml) was added to a mixture of potassium carbonate (3.4 g, 24.8 mmol) and 8-hydroxy-2-(dipropylamino)tetralin (3.06 g, 12.4 mmol) in dichloromethane (300 ml) kept at −70° C. The cooling bath was removed and stirring was continued overnight. The mixture was extracted with an ice-cold saturated aqueous solution of potassium carbonate. The organic layer was dried (potassium carbonate), filtered, and concentrated. The residue was purified on an alumina column eluted with ether/light petroleum 1:8 to afford 5.01 g of an oil that was converted into the hydrochloride. Recrystallization from ethanol/ether gave 5.01 g (97%) of pure 2-(dipropylamino)-8-[(trifluoromethylsulfonyl)oxy]tetralin hydrochloride.

(+)-(R)-2-(Dipropylamino)-8-(trifluoromethylsulfonyloxy)tetralin and (−)-(S)-2-(Dipropylamino)-8-(trifluoromethylsulfonyloxy)tetralin were prepared similarly from the respective enantiomers of 8-hydroxy-2-(dipropylamino)-tetralin which may be obtained in high yields and optical purities.

Example 2

(±)-8-Acetyl-2-(dipropylamino)tetralin hydrochloride. A mixture of 2-(dipropylamino)-8-[(trifluoromethylsulfonyl)-oxy]tetralin (455 mg, 1.2 mmol), tetramethylstannane (257 mg, 1.44 mmol), lithium chloride (158 mg, 3.7 mmol), dichloro[1,1'-bis(diphenylphosphino)ferrocene]palladium (II) (PdCl$_2$(dppf); 61 mg, 0.07 mmol), molecular sieves (4 Å; 120 mg) and dimethylformamide (10 ml) was stirred under an atmosphere of carbon monoxide for 14 h at 90° C. The catalyst was filtered and the filtrate was partitioned between water and ether. The organic layer was dried (sodium sulfate) and concentrated in vacuo. The residue was purified by chromatography on an alumina column eluted with ether/light petroleum 1:16. Pure fractions were pooled and concentrated and the resulting oil was treated with ethereal hydrogen chloride to afford 158 mg (70%) of pure 8-acetyl-2-(dipropylamino)tetralin hydrochloride, which could be recrystallised from CHCl$_3$ and diethylether. Mp 125°–127° C.

Example 3

(±-Methyl 2-(dipropylamino)tetralin-8-carboxylate hydrochloride

A mixture of 2-(dipropylamino)-8-[(trifuloromethylsulfonyl)-oxy]tetralin (3.5 g, 9.2 mmol), triethylamine (1.86 g, 18.4 mmol), palladium(II)acetate (62 mg, 0.28 mmol), 1,1'-bis-(diphenylphosphino)ferocene (306 mg, 0.55 mmol), methanol (5.7 g, 184 mmol), and dimethylsulfoxide (70 ml) was stirred overnight under a positive pressure of carbon monoxide. The mixture was partitioned between a saturated aqueous sodium chloride solution and ether. The organic layer was dried (sodium sulfate) and concentrated. The residue was purified by chromatography on an alumina column eluted first with ether/light petroleum 1:16. Pure fractions were pooled and concentrated. The residual oil was converted into the hydrochloride. Re-crystallization from diethylether/chloroform gave 2.08 g(92%) of methyl 2-(dipropylamin)tetralin-8-carboxylate hydrochloride, mp 136°–137° C.

Example 4

(±)-8-Carboxy-2-(dipropylamino)tetralin

A solution of methyl 2-(dipropylamino)tetralin-8-carboxylate hydrochloride (1.5 g, 4.6 mmol), sodium hydroxide (736 mg, 18.4 mmol), methanol (25 ml) and water (4 ml) was stirred overnight. The methanol was evaporated. Concentrated hydrochloric acid was added until the pH became about 6. The solution was extracted with chloroform. The organic layer was dried (sodium sulfate) and concentrated to give 1.23 g (97%) of pure 8-carboxy-2-(dipropylamino)tetralin as an oil. The hydrochloride melts at 245°–247° C., which could bse recrystallised from methanol/diethylether.

Example 5

(±)-8-Acetyl-2-(dipropylamino)tetralin hydrochloride

A 5% solution of methyl lithium in ether (0.6 ml, 0.96 mmol) was added to a chilled slurry of (±)-8-Carboxy-2-(dipropylamino)tetralin hydrochloride (100 mg, 0, 32 mmol) in ether. The mixture was stirred at room temperature and under nitrogen for three days. Water was added carefully and the mixture was extracted with ether. The organic layer was dried (potassium carbonate) and concentrated. The residue was purified by chromatography on an alumina column eluted with ether/light petroleum 1:4. The pure fractions were pooled, concentrated and converted into the hydrochloride. Recrystallization from acetonitrile/ether gave 55 mg (56%) of pure 8-acetyl-2-(dipropylamino)tetralin hydrochloride.

Example 6

(+)-8-Acetyl-2-(dipropylamino)tetralin hydrochloride

A mixture of (+)-2-(propylamino)-8-[(trifluoromethylsulfonyl)oxyltetralin (300 mg, 0.79 mmol), tetramethylstannane (167 mg, 0.95 mmol), lithium chloride (104 mg, 2.5 mmol), dichloro[1,1'-bis(diphenylphosphino)ferrocene]palladium(II) [PdCl$_2$(dppf)] (40 mg, 0.047 mmol), molecular sieves (4Å; 120 mg), 2,6-di-t-butyl-4-methylphenol (catalytic amounts) in dimethylformamide (6 ml) was stirred under an atmosphere of carbon monoxide for 20 h at 90° C. The catalyst was filtered off and the filtrate was partitioned between water and ether. The organic layer was dried (sodium sulfate) and concentrated in vacuo. The residue was purified by chromatography on an alumina column eluted with ether/-light petroleum 1:16. Pure fractions were pooled and concentrated to give 120 mg (42%) of (+)-8-acetyl-2-(dipropylamino)tetralin as an oil.

Example 7

(−)-8-Acetyl-2-(dipropylamino)tetralin hydrochloride

A mixture of (−)-2-(dipropylamino)-8-[(trifluromethylsulfonyl)oxyl]tetralin (910 mg, 2.4 mmol), tetramethylstannane (514 mg, 2.88 mmol), lithium chloride (315 mg, 7.44 mmol), dichloro[1,1'-bis(diphenylphosphino)ferrocene]-palladium(ii) [PdCl$_2$(dppf)] (12 mg, 0.144 mmol), molecular sieves (4 Å; 240 mg), 2,6-di-t-butyl-4-methylphenol (catalyst) in dimethylformamide (20 ml) was stirred under an atmosphere of carbon monoxide for 18 h at 90° C. The catalyst was filtered off and the filtrate was partitioned between water and ether. The organic layer was dried (sodium sulfate) and concentrated. The residue was chromatographed on an alumina column eluted with ether/light petroleum 1:16. Pure fractions were pooled and concentrated. The resulting oil was converted into the hydrochloride which was recrystallised from chloroform and ether to afford 323 mg (44%) of pure (−)-8-acetyl-2-(dipropylamino)tetralin hydrochloride, mp: 114°–116° C. $[\alpha]_D$:−123.2° C. (c 1.0, MeOH).

Example 8

(±)-8-benzoyl-2-(dipropylamino)tetralin hydrochloride

A mixture of racemic 2-(dipropylamino)-8-[(trifluoromethylsulfonyl)oxy]tetralin (200 mg, 0.52 mmol), phenyltrimethylstannane (154 mg, 0.64 mmol), lithium chloride (69 mg, 1,6 mmol), dichloro[1,1'-bis(diphenylphophino)ferocene]palladium(II) [PdCl$_2$(dppf)] (26 mg, 0.032 mmol), 2.6-di-t-butyl. 4 methylphenol (catalyst), and molecular sieves (4 Å; 40 mg) in dimethylformamide was stirred at 110° C. under an atmosphere of carbon monoxide for 15 h. The mixture was partitioned between water and ether. The organic layer was dried (sodium sulfate) and concentrated in vacuo. The residue was chromatographed on an alumina column eluted with ether/light petroleum 1:16. Pure fractions were pooled and cincentrated. The resulting oil was treated with ethereal hydrogen chloride to afford 100 mg (52%) of pure (+)-8-benzoyl-2-(dipropylamino)tetralin hydrochloride. Mp: 147.5°–150° C.

Example 9

(±)-8-(1-oxopentyl)-2-(dipropylamino)tetralin

A mixture of 2-(dipropylamino)-8-[(trifluoromethylsulfonyl)-oxy]tetralin hydrochloride (216 mg, 0.52 mmol), tetrabutylstannane (218 mg, 0.64 mmol), triethylamine (105 mg, 1.04 mmol), lithium chloride (68 mg, 1.6 mmol), dichloro[1,1'-bis(diphenylphophino) ferrocene] palladium(II) [PdCl$_2$(dppf)](26 mg, 0.03 mmol), 2.6-di-t-butyl-4-methylphenol (catalytic amounts), and molecular sieves (4 Å; 40 mg) in dimethyl formamide (5 ml) was stirred under an atmosphere of carbon monoxide for 20 h at 120° C. The mixture was filtered and the filtrate was partitioned between water and ether. The organic layer was dried (sodium sulfate) and concentrated in vacuo. The residue was purified by chromatography on an alumina column eluted with ether/light petroleum 1:16. Pure fractions were pooled and concentrated. The resulting oil was treated by ethereal oxalic acid to afford 150 mg (71%) oxalate as an oil.

Example 10

(±)-8-Phenyl-2-(dipropylamino)tetralin oxalate

A mixture of racemic 2-(dipropylamino)-8-(trifluoromethylsulfonyloxy)tetralin (450 mg, 1.2 mmol), trimethylphenylstannane (433 mg, 1.8 mmol), tetrakis(triphenylphosphine)-palladium (0) (69 mg, 0.06 mmol), lithium chloride (153 mg, 3,6 mmol) and 2.6-di-t-butyl-4-methylphenol (catalyst) in 15 ml of dioxane and and 1.5 ml of dimethylformamide was stirred at 105° C. in a resealable flask for 3 days. The mixture was filtered (celite), concentrated and partioned between saturated potassium carbonate and ether. The organic layer was dried over potassium carbonate and concentrated in vacuo. The residue was chromatographed on an alumina column eluted first with petroleum, followed by ether/light petroleum (1:40) and then ether/light petroleum (1:20). Pure fractions were collected and treated with ethereal oxalic acid affording 232 mg (48%) of (±)-8-phenyl-2-(dipropylamino)tetralin oxalate, m.p. 162°–163° C.

(+)-(R)-8-Phenyl-2-(dipropylamino)tetratin and (−)-(S)-8-phenyl-2-(dipropylamino)tetratin were prepared similarly from (R)-and (S)-2-(dipropylamino)-8-(trifluoromethylsulfonyloxy)tetralin, respectively.

Example 11

(±)-8-(2-Furanyl)-2-(dipropylamino)tetralin oxalate.

A mixture of racemic 2-(dipropylamino)-8-(trifluoromethylsulfonyloxy)-tetralin (100 mg, 0.26 mmol), furan-2-yltrimethylstannane (75 mg, 0.32 mmol), dichloro [1,1'-bis(di-phenylphosphino)-ferocene]palladium(II) (12 mg, 0.014 mmol), lithium chloride (69 mg, 1.6 mmol), molecular sieves (60 mg) and 2,6-di-t-butyl-4-methylphenol (catalyst) in 3 ml of dimethylformamide was stirred at 90° C. in a sealed flask overnight. The mixture was filtered (Celite) and partitioned between a saturated sodium bicarbonate solution and ether. The ether layer was dried (potassium carbonate), filtered and concentrated in vacuo. The residue was chromatographed on alumina with ether/light petroleum (1:16) as eluant. Pure fractions were collected and treated with ethereal oxalic acid to give a white powder which was recrystallized from MeOH/ether affording 36 mg (36%) of (±)-8-(furan-2-yl)-2-(dipropylamino)-tetralin oxalate, m.p. 113°–114° C.

Example 12

(±)-8-(Benzofuran-2-yl)-2-(dipropylamino)tetralin oxalate

A mixture of racemic 2-(dipropylamino)-S-(trifluoromethylsulfonyloxy)tetralin (400 mg, 1.04 mmol), benzofuran-2-yltrimethylstannane (444 mg, 1.6 mmol), tetrakis(triphenylphosphine) palladium(0) (60 mg, 0.052 mmol), lithium chloride (140 mg, 3.24 mmol) and 2,6-di-t-butyl-4-methylphenol (catalyst) in 12 ml of 1,4-dioxane and 1.2 ml of dimethylformamide was stirred at 105° C. in a sealed flask for 3 days.

The mixture was filtered (Celite), concentrated and partitioned between a saturated potassium carbonate solution and ether. The ether layer was dried (potassium carbonate), filtered and concentrated. The residue was chromatographed on an alumina column eluted with light petroleum, followed by ether/light petroleum (1:40), ether/light petroleum (1:20) and ether. Pure fractions were collected and treated with ethereal oxalic acid to give 220 mg (48%) of (±)-8-(benzofuran-2-yl)-2-(dipropylamino)tetralin oxalate, m.p. 168°–170° C.

Example 13

(1S,2R)-1-Methyl-2-(Dipropylamino)-8-(trifluoromethylsulfonyloxy)tetralin.

A solution of (1S,2R)-1-methyl-8-methoxy-2-(dipropylamino)tetralin hydrochloride (J. Med. Chem. 1987, 30, 2105–2109) in freshly distilled 48% HBr was stirred at 120° C. for 3 h. The reaction mixture was evaporated and partitioned between an ice-cold saturated sodium bicarbonate solution and dichloromethane. The organic layer was dried over sodium sulfate, filtered and concentrated. The residue of crude (1S,2R)-8-hydroxy-1-methyl-2-(dipropylamino)tetralin was used directly.

To the mixture of demethylated starting material and potassium carbonate (1.0 g, 6.6 mmol) in 20 mL of dichloromethane was added the solution of triflic anhydride (1.3 g, 4.4 mmol) in 10 mL if dichloromethane at –78° C. during 15 min under nitrogen. The reaction was kept at room temperature with stirring overnight. The reaction mixture was concentrated and partitioned between a saturated potassium carbonate solution and ether. The organic layer was dried over potassium carbonate, filtered and concentrated. The residue was chromatographed on an alumina column with ether/light petroleum (1:8) as eluant. Pure fractions were collected and concentrated to afford 744 mg (86%) of the free base of the triflate.

Example 14

(1S,2R)-8-Benzoyl-1-methyl-(dipropylamino)tetralin hydrochloride

A mixture of (1S,2R)-1-methyl-2-(dipropylamino)-8-(trifluoromethylsulfonyloxy)tetralin (100 mg, 0.25 mmol), (Example 13) phenyltrimethylstannane (80 mg, 0.33 mmol), lithium chloride (33 mg, 0.77 mmol),dichloro[1,1-bis (diphenylphosphino)ferocene]palladium(II) (13 mg, 0.015 mmol), 2.2-di-t-butyl-4-methylphenol (catalyst) and molecular sieves (4 Å; 40 mg) in 3 ml of dimethylformamide was stirred at 90° C. under carbon monoxide overnight. The reaction mixture was filtered (Celite), concentrated and chromatographed on an alumina column eluted with ether/ light petroleum (1:16). Pure fractions were collected and treated with ethereal HCl to give a white solid which was recrystallised from chloroform and ether affording 45 mg (47%) of (1S,2R)-8-benzoyl-1-methyl-2-(dipropylamino) tetralin hydrochloride, mp: 147.5°–150° C.

Pharmacology

Pharmacological Treatment of Depression in Man

Evidence is available that in depressed patients the nerurotransmission in the central nervous system (CNS) may be disturbed. These disturbances appear to involve the neurotransmitters noradrenaline (NA) and 5-hydroxytryptamine (5-HT). The drugs most frequently used in the treatment of depression are considered to act by improving the neurotransmission of either or both of these physiological agonists. Available data suggest that the enhancement of 5-HT neurotransmission will primarily improve the depressed mood and anxiety, whereas the enhancement of noradrenaline neurotransmission will rather improve the retardation symptoms occurring in depressed patients. In recent years many efforts have been made to develop new drugs with high selectivity for the improvement of the 5-HT neurotransmission in the CNS.

The mechanism of action for the drugs generally used today in the therapy of mental depression is indirect, i.e. they act by blocking the reuptake of the neurotransmitters (NA and/or 5-HT) released from nerve terminals in the CNS, thus increasing the concentration of these transmitters in the synaptic cleft and hence restoring an adequate neurotransmission.

A fundamentally different way to regulate the neurotransmission in the central 5-HT-neurons would be to use a direct 5-HT-receptor agonists/antagonists. In order to minimize side effects, a selectivity for this kind of receptors would then be preferable.

Surprisingly, we have found that a group of compounds of the formula I have selective, direct stimulating effect on, or blockade of a subgroup of central 5-HT receptors. Another observation is that some of these compounds have a particularly good oral bioavailability. In order to evaluate the affinity for this subgroup of/the 5-HT-receptors, the effects on various receptors in rat brain were measured in vitro using receptor assays (Ki nM).

In Vitro Test: Receptor Binding Assay $5HT_{1A}$ binding assay. Cerebral cortex + hippocampus from each rat was dissected and homogenized in 15 ml ice-cold 50 mM Tris-HCl buffer 4.0 mM $CaCl_2$ and 5.7 mM ascorbic acid, pH 7.5 with an Ultra-Turrax (Janke & Kunkel, Staufen, FRG) for ten s. After centrifugation for 12.5 min at 17,000 rpm (39,800×g in a Beckman centrifuge with a chilled JA-17 rotor (Beckman, Palo Alto, Calif., USA), the pellets were resuspended in the same buffer and homogenization and centrifugation repeated. To each pellet 5 ml ice-cold 0.32M sucrose were added and homogenized for 5 sec. These samples were kept frozen at –70° C. When used they were diluted with the buffer to 8 mg tissue/ml and homogenized for 10 sec.

The tissue homogenates were incubated for ten min at 37° C. and then supplied with 10 µM pargyline followed by reincubation for 10 min.

The binding assay followed that described by Peroutka, J. Neurochem. 47, 529–540, (1986). The incubation mixture (2 ml) contained $^3$H-8-OH-DPAT (0.25 to 8 nM), 5 mg/ml tissue homogenate in 50 mM Tris-HCl buffer containing 4.0 mM $CaCl_2$ and 5.7 mM ascorbic acid, pH 7.5. Six different concentrations of $^3$H-8-OH-DPAT were analyzed. Binding experiments were started by the addition of tissue homogenate and followed by incubation at 37° C. for ten min. The incubation mixtures were filtered through Whatman GF/B glass filters with a Brandel Cell Harvester (Gaithersburg, Md., USA). The filters were washed twice with 5 ml ice-cold 50 mM Tria-HCl buffer, pH 7.5, and counted with 5 ml Ready-solv HP (Beckman) in a Beckman LS 3801 scintillation counter. Non-specific binding was measured by the addition of 10 µM 5-HT to the reaction mixture. The binding data was processed by non-linear least squares computer/ analysis (Munson and Rodbard, Anal. Biochem. 107, 220–239, (1980).

TABLE 1

| Receptor-binding | |
|---|---|
| Example no. | Ki (nm) |
| 2 | 0.9 |
| 6 | 1.7 |
| 11 | 1.5 |

We claim:

1. A compound of the formula:

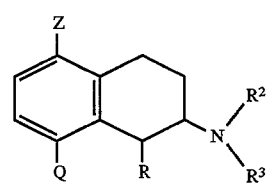

or an enantiomer or physiologically acceptable salt thereof, wherein
R is hydrogen;
Z is halogen;
Q is $COR^1$ or a 5-membered aryl which may contain 1 heteroatom selected from O or S and which may optionally be substituted by one or more substituents independently selected from halogen, CN, $CF_3$, $C_1$–$C_6$ alkyl, $C_2$–$C_6$ alkenyl and lower alkoxy;

$R^1$ is $C_1$–$C_6$ alkyl;

$R^2$ is hydrogen, methyl, ethyl, n-propyl, i-propyl or cyclopropyl; and $R^3$ is methyl, ethyl, n-propyl, i-propyl or cyclopropyl.

2. A compound according to claim 1, wherein Q is thienyl or furanyl.

3. A compound according to claim 1, wherein Q is $COR^1$.

4. The compound according to claim 3, wherein $R^1$ is methyl.

5. A pharmaceutical composition comprising a compound according to claim 1, an enantiomer or a physiologically acceptable salt thereof in a pharmaceutically acceptable carrier.

6. A method for treatment of disorders of the central nervous system associated with 5-$HT_{1A}$ receptor activity, comprising administering to a mammal in need thereof a therapeutically effective amount of a compound defined in any one of claims 2, 1, 3 and 4.

7. A method according to claim 6 for treatment of a disorder selected from the group consisting of depression, and anxiety.

* * * * *